United States Patent
Lowe et al.

[11] Patent Number: 6,106,475
[45] Date of Patent: *Aug. 22, 2000

[54] DEVICE FOR USE IN TEMPORARY INSERTION OF A SENSOR WITHIN A PATIENT'S BODY

[75] Inventors: Robert I. Lowe; Anthony P. Furnary, both of Portland, Oreg.

[73] Assignee: Tobo, LLC, Portland, Oreg.

[ * ] Notice: This patent is subject to a terminal disclaimer.

[21] Appl. No.: 09/046,369

[22] Filed: Mar. 23, 1998

Related U.S. Application Data

[63] Continuation-in-part of application No. 08/672,484, Jun. 26, 1996, Pat. No. 5,775,328.

[51] Int. Cl.[7] .................................................. A61B 8/00
[52] U.S. Cl. ........................................... 600/462; 600/466
[58] Field of Search ................................. 604/22, 27, 28, 604/916; 600/458, 462, 466, 467; 601/4

[56] References Cited

U.S. PATENT DOCUMENTS

| | | | |
|---|---|---|---|
| 3,878,849 | 4/1975 | Muller et al. | 128/349 |
| 4,100,309 | 7/1978 | Micklus et al. | 427/2 |
| 4,408,612 | 10/1983 | Utsugi | 128/660 |
| 4,671,295 | 6/1987 | Abrams et al. | 128/663 |
| 4,722,347 | 2/1988 | Abrams et al. | 128/663 |
| 4,886,059 | 12/1989 | Weber | 128/207.15 |
| 4,947,854 | 8/1990 | Rabinovitz et al. | 128/662.04 |
| 5,205,292 | 4/1993 | Czar et al. | 128/662.03 |
| 5,284,146 | 2/1994 | Czar et al. | 128/662.03 |
| 5,291,896 | 3/1994 | Fonger et al. | 128/713 |
| 5,331,947 | 7/1994 | Shturman | 126/4 |
| 5,335,663 | 8/1994 | Oakley et al. | 128/662 |
| 5,443,445 | 8/1995 | Peters et al. | 604/27 |

*Primary Examiner*—George Manuel
*Attorney, Agent, or Firm*—Chernoff, Vilhauer, McClung & Stenzel, LLP

[57] ABSTRACT

A device for use in placing a non-sterile sensor probe such as an ultrasound scanning transducer in a desired position within a patient's body, with a probe-receiving tube having a closed distal end so that a probe inserted within the tube through an open proximal end located outside the patient's body is isolated from contact with or contamination of the interior of the patient's body. The probe-receiving tube is attached to and extends alongside an elongate support member which aids in placement of the probe-receiving tube in a location proximate an organ to be observed by use of a sensor probe in the probe-receiving tube. The elongate support tube may be a chest drain tube.

21 Claims, 5 Drawing Sheets

DEVICE FOR USE IN TEMPORARY INSERTION OF A SENSOR WITHIN A PATIENT'S BODY

This is a continuation-in-part of U.S. patent application Ser. No. 08/672,484, filed Jun. 26, 1996 now U.S. Pat. No. 5,775,328.

BACKGROUND OF THE INVENTION

The present invention relates to placement of sensors within a patient's body, and in particular relates to facilitating repeated placement of a non-sterile sensor, such as an ultrasound transducer, into a patient's body in a minimally invasive and sterile manner.

It is frequently desirable to obtain information regarding the size, shape, and function of internal body organs by the use of ultrasound echo imaging. For example, it is desirable to evaluate the performance of a patient's heart after cardiac surgery. In the time immediately after such surgery, patients frequently have significant cardiac functional problems, and visualization and examination of the heart by ultrasound echo imaging may be of critical value. Currently, transthoracic and transesophageal echocardiography are performed as manners of observing the heart. These are not entirely desirable, however, as the second requires sedation and presents risks of trauma to the esophagus and the images obtained by the first are of poor quality after cardiac surgery.

Fonger et al. U.S. Pat. No. 5,291,896 discloses a sterile cardiac probe inserted through an open-ended lumen of a flexible chest drain tube having one end extending into the thoracic cavity of a patient. The probe is surgically fastened to the aorta or the pulmonary artery of the patient in order to obtain information relating only to the volume of flow of blood through such vessels.

Czar et al. U.S. Pat. No. 5,205,292 discloses a removable surgically implanted sterile transducer for attachment to a blood vessel in order to evaluate the volume of blood flow in the vessel.

Abrams et al. U.S. Pat. No. 4,671,295 discloses a method and apparatus for measuring cardiac output through the use of a transducer introduced into the patient's trachea to transmit and receive ultrasound waves and evaluate the flow of blood in the ascending aorta through the use of Doppler frequency differences.

Weber U.S. Pat. No. 4,886,059 discloses an endotracheal tube including a transducer assembly disposed to transmit ultrasound waves in selected directions through the tracheal wall to collect Doppler data for blood flow velocity calculation and to calculate the diameter of the artery.

None of the devices disclosed in the patents discussed above, however, provides for placement of a non-sterile sensor such as an ultrasound transducer in a desired position within a sterile body cavity of a patient quickly, easily and repeatedly, nor does any of them provide a way of obtaining scanned ultrasound two-dimensional echo images of internal organs without having to transmit the ultrasound waves into the body from an external location.

What is desired, then, is a device and a method for its use in permitting a non-sterile sensor such as an ultrasound scanning transducer to be introduced into a body cavity of a patient quickly and easily in a sterile fashion, and without performing additional surgical procedures or sedation as part of the introduction of the transducer. It is also desired to provide for removal and later temporary reintroduction of a non-sterile sensor without further surgical procedures or sedation.

SUMMARY OF THE INVENTION

The present invention provides an answer to the need explained above by providing a sterile probe-receiving tube which makes available a sterilely protected non-sterile space within a patient's body where a sensor probe may be inserted when necessary, either to be left in place or removed and reinserted later, as necessary. In accordance with the invention such a probe-receiving tube is supported by an elongate support member, which may have other supportive functions, attached to and extending along at least a distal portion of the probe-receiving tube, and a proximal portion of the probe-receiving tube is available outside the patient's body as an entrance through which to insert a non-sterile probe into the interior of the patient's body. In one embodiment of the invention a proximal portion of the elongate support member is available outside the patient's body for use if necessary to adjust the location of the probe enclosed within the probe-receiving tube attached to it.

In a device which is one embodiment of the invention the elongate support member is in the form of a chest drain tube placed within the thoracic cavity of a cardiac surgery patient prior to closing the patient's chest, with the proximal portion of the device being located externally of the patient's abdomen and the distal portion of the device extending through an opening in the abdominal wall and thence toward the patient's heart, so that the probe-receiving tube is available in a desired position to provide an ultrasound two-dimensional echo image of the patient's heart or continuous-wave pulse gated, and color flow Doppler ultrasound data during the post-surgery period when it is critical to evaluate the function of the heart.

In a preferred embodiment of the invention a conduit may be provided through which to introduce an acoustic coupling medium into the distal portion of the probe-receiving tube to enable a sensor utilizing sound waves, such as an ultrasound transducer probe, to be operated efficiently. Since the distal end of the probe-receiving tube of a device according to the invention is closed, the internal space within the probe-receiving tube is isolated from the interior of the patient's body cavity, and introduction of a non-sterile sensor probe or of material introduced through the conduit as an acoustic coupling agent cannot result in contamination of the patient's body cavity.

In a device that is another embodiment of the invention a support member includes a separable part and may include a cutting device by which the separable part can be removed easily from the support member and the probe-receiving tube once it is located in a desired position, leaving a support member of reduced size attached to the probe-receiving tube.

In accordance with the method of the invention a sensor probe can be placed quickly and easily in a desired location within a patient's body by inserting it into the patient's body through the probe-receiving tube at any time after the probe-receiving tube, supported by the elongate supporting member, has been installed.

Thus, according to the method of the invention, a non-sterile ultrasound probe may be inserted through the probe-receiving tube into a position proximate an internal organ such as a patient's heart to obtain an ultrasound echo image of the organ, as for providing an ultrasound image of the heart at a time subsequent to the completion of cardiac surgery.

Once the probe-receiving tube is in a required location, part of a support member is removed in accordance with the method of the invention, and the probe-receiving tube is left in place, supported by a support member of reduced size, but ready to receive a sensor probe quickly when needed.

The foregoing and other objectives, features, and advantages of the invention will be more readily understood upon consideration of the following detailed description of the invention, taken in conjunction with the accompanying drawings.

DETAILED DESCRIPTION OF THE PREFERRED EMBODIMENT

Figures 1, 4, 7:
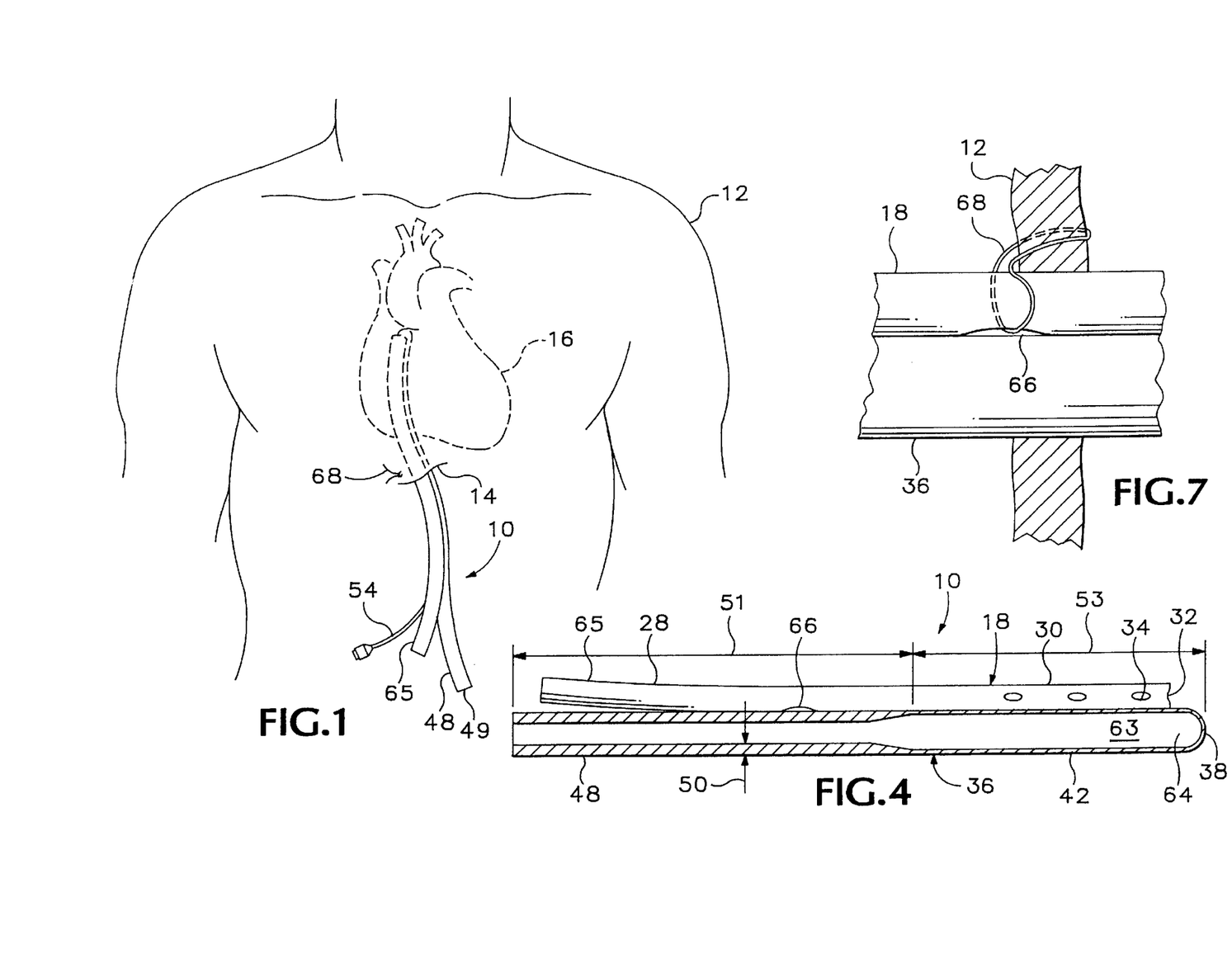
FIG. 1 is a simplified view of a patient's torso, showing a device embodying the present invention in place.
FIG. 4 is a side elevational view of the combined chest drain tube and probe-receiving tube shown in FIGS. 1–3, with the probe-receiving tube shown in sectional view.
FIG. 7 is a simplified view showing a short portion of the combined drain tube and probe-receiving tube shown in FIG. 1, with the combined tubes extending through the abdominal wall of a patient, and showing a suture holding the drain tube in its required location.

Referring now to the drawings which form a part of the disclosure herein, an access-providing device 10 embodying the present invention is shown in place in a cardiac surgery patient 12, with the device extending into the interior of the thoracic cavity of the patient 12 through a surgical opening 14 beneath the sternum, so that a sensor can later be positioned within the device 10 in a desired location within the thoracic cavity of the patient, in order to obtain, for example, an ultrasound image of the patient's heart 16.

Figures 2, 3, 5, 6:
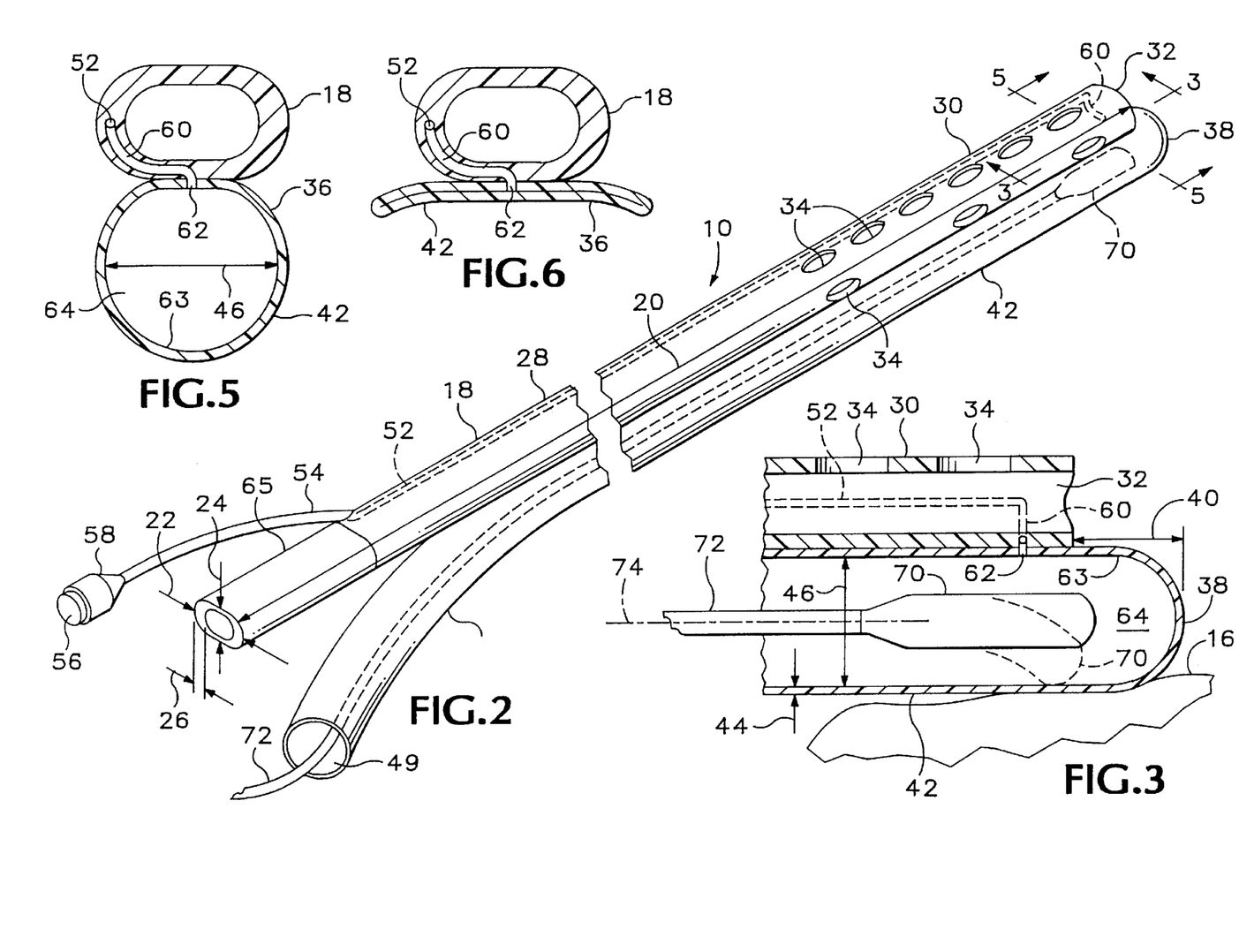
FIG. 2 is a perspective view of a combined chest drain tube and probe-receiving tube according to the present invention.
FIG. 3 is a sectional view of part of a distal end portion of the combined chest drain tube and probe-receiving tube shown in FIG. 2.
FIG. 5 is a sectional view, taken along line 5—5 of FIG. 2.
FIG. 6 is a sectional view taken along line 5—5 of FIG. 2, with the distal end portion of the probe-receiving tube in a collapsed condition.

As shown in greater detail in FIGS. 2, 3, and 4, the device 10 includes a chest drain tube 18, preferably of a type manufactured by Axiom Medical, Inc., of Rancho Dominguez, Calif. Such a chest drain tube 18 is of a resiliently flexible silicone rubber material which is clear and translucent and suitable for biomedical applications. One satisfactory material for the drain tube 18 has, for example, a Shore A hardness of 60±5 durometer, at least 1100 psi tensile strength, at least 600% elongation, and tear-resistance of at least 130 pounds per inch. These characteristics are not critical, but what is necessary is for the drain tube 18 to be suitable for biomedical use and to be somewhat flexible. The chest drain tube 18 shown herein as an example has a length 20 of about 445 mm and is oval in cross-section, having a width 22 of about 1.8 cm and a height 24 of about 9 mm, but these dimensions are not critical to the present invention. A maximum wall thickness 26, at one end of the oval cross-section shape, may be about 2.5 mm.

A proximal portion 28 of the chest drain tube 18 normally remains outside the body of a patient, while the drain tube 18 extends through the surgical opening 14 and a distal end portion 30 is in position in the pericardial space to remove blood following open heart surgery. The blood can enter into the lumen of the chest drain tube through the open distal end 32 and several openings 34 defined through the wall of the distal end portion 30.

Extending along and attached to the distal end portion 30 and a part of the proximal portion 28 is a probe-receiving tube 36, for which the chest drain tube 18 acts as an elongate support member. The probe-receiving tube 36 is of a biologically compatible and ultrasound translucent material such as a silicone rubber similar to that of the chest drain tube 18, in a preferred embodiment of the invention. The probe-receiving tube 36 has a thin, flexible wall and is generally oval or circular in cross-section, as may be seen best in FIG. 5. It has a closed distal end 38 which may be generally hemispherical, and which extends beyond the open distal end 32 of the drain tube 18 by a distance 40 of at least about 5 mm and preferably about 5 mm. A distal portion 42 and the closed distal end 38 of the probe-receiving tube 36 have a wall thickness 44 of about 0.4 mm and an inside diameter 46 of about 16 mm (36 French). The wall thickness 44 is small enough that it allows the distal portion 42 of the probe-receiving tube 36 to collapse easily or to conform easily to the shape of an object pressing against its outside surface. As may be seen most clearly in FIG. 4, a proximal portion 48 of the probe-receiving tube 36 has a length 51 of about 28 cm and has a greater wall thickness 50, for example 1.2 mm so that it has a greater tendency to retain its circular shape, for reasons which will be made apparent presently.

The distal portion 42 has a length 53 of about 24 cm, for example. The distal portion 42 and a part of the proximal portion 48 of the probe-receiving tube 36 extend along and are securely adhered to the chest drain tube 18, as shown best in FIGS. 4, 5 and 6.

A small tubular conduit 52 is defined within the wall of the chest drain tube 18 and communicates with a branch tube 54 extending away from the proximal portion 28. The branch tube 54 may be closed off tightly, as by a plug 56 fitting in an end coupling 58 which may be formed as an integral part of the branch tube 54. Near the distal end 32 of the drain tube 18, an interconnecting portion 60 of the small conduit 52 extends circumferentially of the drain tube 18 within its wall to an internal port 62, shown in FIGS. 3, 5 and 6, opening into the interior space 64 within the probe-receiving tube 36.

Preferably, the interior surface 63 of the probe-receiving tube 36, defining an interior space 64, is coated with a friction-inhibiting material which makes the interior surface very slippery when it is wetted by water or blood. This material resists adhesion and clotting of blood and is also used on the interior and exterior surfaces of the chest drain tube 18. A coating material suitable for this purpose is a polyvinyl-pyrollidone-polyurethane interpolymer, as disclosed in Micklus et al. U.S. Pat. No. 4,100,309, for example, available from Axiom Medical, Inc. of Rancho Dominguez, Calif. under the trademark Clot-Stop.

The proximal end part 65 of the proximal portion 28 of the chest tube 18, extending proximally from the point of insertion of the branch tube 54, does not include a lumen corresponding to small conduit 52. The proximal end part 65 may be formed as a separate piece of similar tubing without such a small lumen, joined to the portion of the chest drain tube 18 which does include the small conduit 52, so that there is no open end of the small conduit 52 exposed to possible contamination.

As shown in FIGS. 4 and 7, a transversely-extending fastener passageway 66 is defined between the chest drain tube 18 and the probe-receiving tube 36, to permit a suture 68, or a similar fastener, to encircle the chest drain tube 18 to fasten it in place where it extends through the surgical opening 14, as shown in FIG. 7, without constricting the probe-receiving tube 36.

Referring once more to FIG. 1, the access-providing device 10 may be used for a patient whose chest has been opened for cardiac surgery, by inserting the distal end part 30 of the drain tube 18, together with the attached distal portion 42 of the probe-receiving tube, through the surgical opening 14 and into the pericardial space within the patient 12. A suture 68 is used to fasten the device 10 in place with the proximal portion 48 of the probe-receiving tube 36 preferably resting against the right ventricle of the patient's heart 16. The openings 34 are thus left available, unobstructed, to provide the required drainage of the pericardial space once the patient's chest has been closed in completion of surgery. The probe-receiving tube 36 is thus kept properly located and available to receive a probe such as a steerable ultrasound transducer probe 70 which can be inserted into the distal end 43 of the probe-receiving tube 36, supported by an encapsulated cable 72 of conventional form. The size of the interior space 64 defined within the probe-receiving tube 36 is ample to admit an ultrasound probe 70 of the size and type well known for use transesophageally in adults, such as a piezoelectric transducer available from Hewlett-Packard, Advanced Technology Laboratory, or Accuson. A transducer probe 70 of smaller size may be utilized if available. The transducer cable 72 is preferably of a type which is controllably bendable and allows the transducer probe 70 to be reoriented to transmit ultrasound vibrations in various directions as illustrated by the position of the transducer probe 70 shown in broken line in FIG. 3. Additionally, the cable 72 and the ultrasound transducer probe 70 may be rotated about the longitudinal axis 74 of the cable 72, to obtain an ultrasound image in a desired direction. The distal end portion 38 of the probe-receiving tube 36, extending beyond the distal end 32 of the drain tube 18, permits unobstructed transmission and reception of the ultrasound waves by the transducer probe 70 in any direction relative to the axis 74.

Preferably, the usual placement of the chest drain tube 18, extending into the body cavity of the patient 12 through the right rectus muscle and fascia in an orientation slightly divergent from vertical, brings the probe-receiving tube 36 into contact with the anterior surface of the epicardium of the right ventricle of the patient's heart 16. The position of the access-providing device 10 can be adjusted by the surgeon during surgery, before closure of the chest, and the suture 68 can be used to keep the entire device 10 in the proper location, to permit repeated insertion and removal of the transducer 70 through the probe-receiving tube 36 so long as the device 10 is left in place.

To assure good acoustic coupling, particularly where the transducer 70 may not be in intimate contact with the interior surface 63 of the probe-receiving tube 36, a quantity of a liquid acoustic coupling medium, such as water, may be introduced into the branch tube 54 through the end coupling 58 to displace air surrounding the transducer probe 70 within the interior space 64.

The greater wall thickness 50 in the proximal portion 48 of the probe-receiving tube 36 provides additional ability to resist collapsing during insertion of a probe such as an ultrasound transducer. This facilitates pushing the probe 70 and its cable 72 into the proper position within the probe-receiving tube 36, without wrinkling the part of the proximal portion 48 that is unattached to the drain tube 18. The portion of the probe-receiving tube 36 which is securely attached alongside the drain tube 18 is less likely to wrinkle and impede insertion of the probe transducer 70, particularly if the interior surface of the probe-receiving tube 36 is coated with the previously-described friction-reducing coating and has been wetted as by insertion of fluid through the branch tube 54 and the small conduit 52. Since the interior space 64 within the probe-receiving tube 36 is entirely isolated from possible contact with the interior of the body of the patient 12, it need not be sterile, and it is possible to insert the ultrasound transducer probe 70 temporarily into the probe-receiving tube 36 at various times as required or desired for observation of the function of the patient's heart following surgery. Therefore, it is not absolutely necessary to keep the proximal end 49 closed and clean.

When the probe 70 and its cable 72 are not located within the interior space 64, the distal portion 48 of the probe-receiving tube 36 is free to collapse under the pressures encountered within the body cavity where the probe-receiving tube is located, as shown in FIG. 6. At the same time, the greater wall thickness 50 keeps the proximal portion of the probe-receiving tube 36 open to receive a transducer probe 70 and cable 72.

When the drain tube and the probe-receiving tube are no longer needed the suture-68 may be removed releasing the device 10 to be withdrawn, and the opening 14 can be closed.

While the invention has been described above in connection with one preferred embodiment, it will be understood that the probe-receiving tube 36 of the invention may be unsupported or supported by an elongate support member of a different construction and can be utilized for repeated temporary insertion and removal of a medical sensor such as an ultrasound transducer probe in different internal cavities of the body of a patient 12 either briefly or over an extended time of as much as several days. The probe-receiving tube of the invention thus can be used in order to scan organs within the patient's body with ultrasound or provide ultrasound transmissions for purposes of obtaining Doppler measurements, either through an opening such as the surgical opening 14, or through a natural orifice of the patient's body, such as the trachea, urethra and bladder, or rectum, so that ultrasound wave propagation to and from the organ is more direct than when transmitted through the patient's skin and layers of external tissue or bones.

Figures 8, 9, 10:
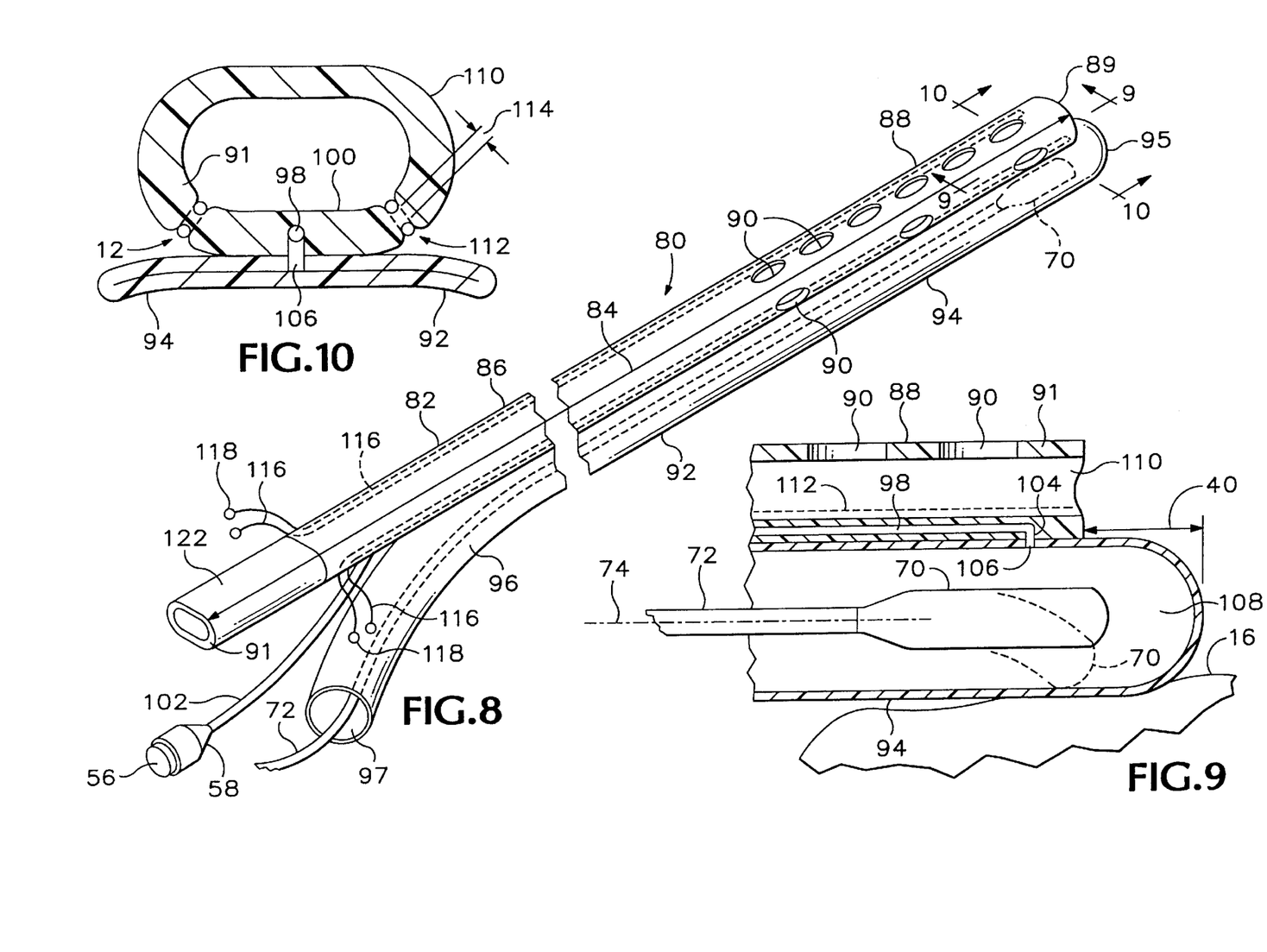
FIG. 8 is a perspective view of a combined chest drain tube and probe-receiving tube which is another embodiment of the present invention.
FIG. 9 is a sectional view of a part of a distal end portion of the combined chest drain tube and probe-receiving tube shown in FIG. 8.
FIG. 10 is a sectional view, taken along line 10—10 of FIG. 8, with the distal end portion of the probe-receiving tube in a collapsed condition.

For example, one such variation is illustrated in the form of an access-providing device 80 shown in FIGS. 8-14. First referring particularly to FIGS. 8, 9, and 10, the device 80 includes a chest drain tube 82 of, for example, a resiliently flexible silicone rubber material which is preferably clear and transparent and suitable for biomedical applications. The chest drain tube 82 has a length 84 and may be oval in cross-section shape, as shown in FIG. 10. The chest drain tube has a proximal portion 86 and a distal end portion 88 with an open end 89 and defines several openings 90 extending through the wall 91 of the distal end portion 88 and communicating with the lumen of the drain tube 82 to allow material to enter the drain tube to be drained from a patient's body cavity.

Extending closely alongside and attached to the chest drain tube 82, along its distal end portion 88 and a part of its proximal end portion 86, is a probe-receiving tube 92 essentially similar to the probe-receiving tube 36 of the access-providing device 10 described above. A distal portion 94 and a part of a proximal portion 96 of the probe-receiving tube 92 are securely adhered to the chest drain tube 82 as by being thermally fused during manufacture of the device 80, with a closed distal end 95 extending a short distance beyond the distal end 89 of the drain tube 82. A proximal end 97 of the probe-receiving tube 92 is open, to receive a sensor probe such as an ultrasound transducer 70 and its cable 72.

A small tubular conduit 98 is similar to the conduit 52 described in connection with the access-providing device 10, but is located in a base portion 100 of the chest drain tube 82. The base portion 100 is the part of the chest drain tube 82 extending along and located most closely adjacent to the probe-receiving tube 92, to which the base portion 100 is directly attached. A branch tube 102, similar to the branch tube 54, extends from the base portion 100 of the chest drain tube 82, near the proximal end 86, and communicates with the small conduit 92. Near the distal end portion 88 of the chest drain tube 82 an interconnecting portion 104 of the small conduit 98 extends through an internal port 106 into the interior space 108 within the probe-receiving tube 92 so that the branch tube 102 and the conduit 98 can be used to supply an acoustic coupling fluid or contrast medium to the space 108.

A separable portion 110 of the chest drain tube 82 is removable from the base portion 100. The separable portion extends longitudinally of the chest drain tube 82 and is delineated by a separation region 112 including an interface between the separable portion 110 and the base portion 100. The material of the drain tube 82 in the separation region 112 is intended to fail more easily than the adjacent portions of the drain tube 82 to allow the separable portion 110 to be removed easily from the base portion 100. The separation region 112 may be defined by appropriately shaping the chest drain tube 82 so that a linear region has a lesser wall thickness, as at 114, and thus has a lesser strength than adjacent portions of the wall 92 of the chest drain tube 82, so that the separable portion 110 can be torn apart from the base portion 100 under a definite force that is small enough not to disturb the location of the distal portion 94 of the probe-receiving tube 92. It may be desirable to initiate such tearing by making a small cut in the drain tube wall in the separation region 112 when it is desired to remove the separable portion 110 from the base portion.

Figures 11, 12:
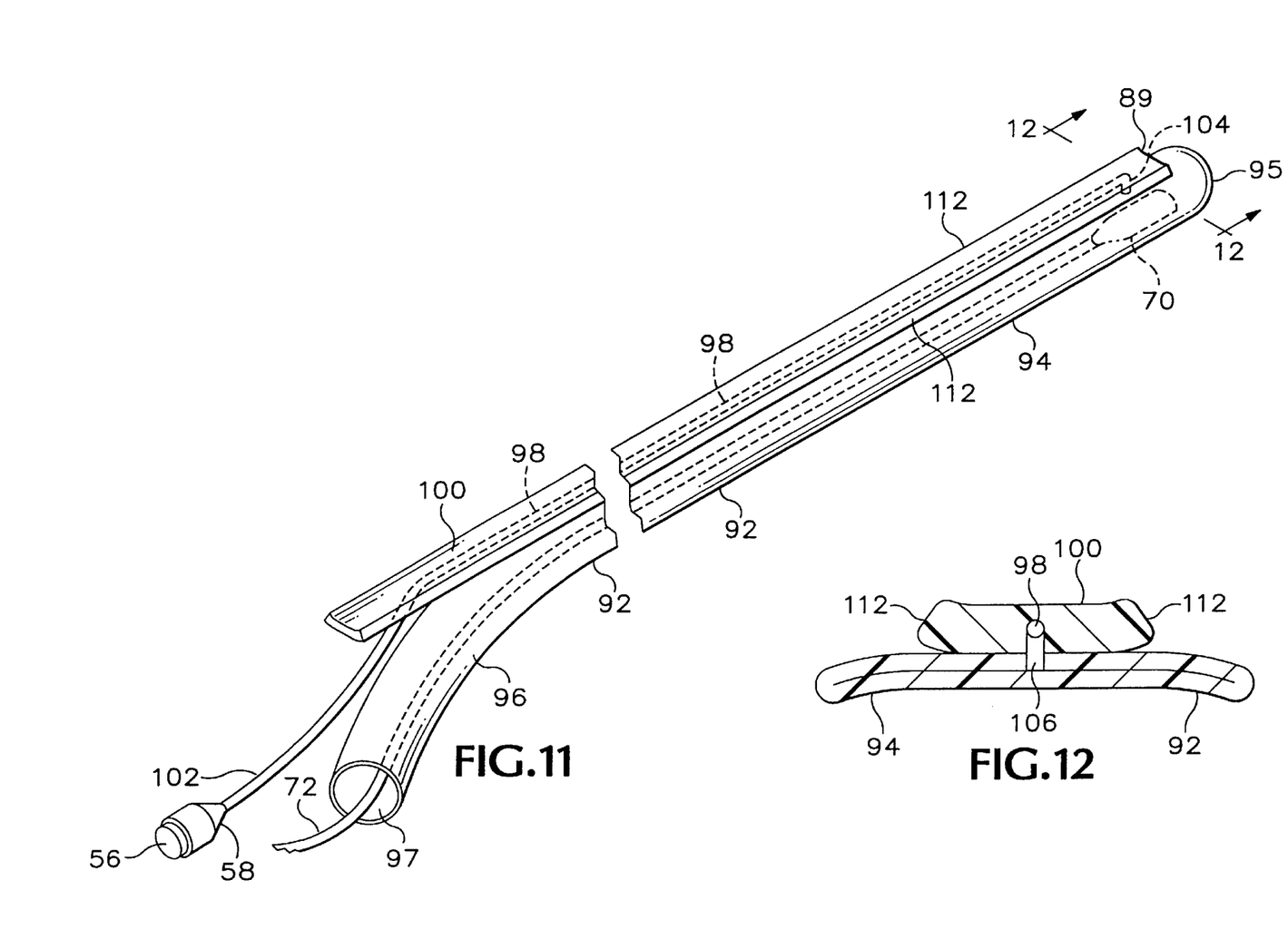
FIG. 11 is a perspective view of the probe-receiving tube and a portion of the chest drain tube shown in FIG. 8, a separable portion having been removed from the chest drain tube in accordance with the present invention.
FIG. 12 is a sectional view taken along line 12—12 of FIG. 11, with the distal end portion of the probe-receiving tube in a collapsed condition.
Figure 13:
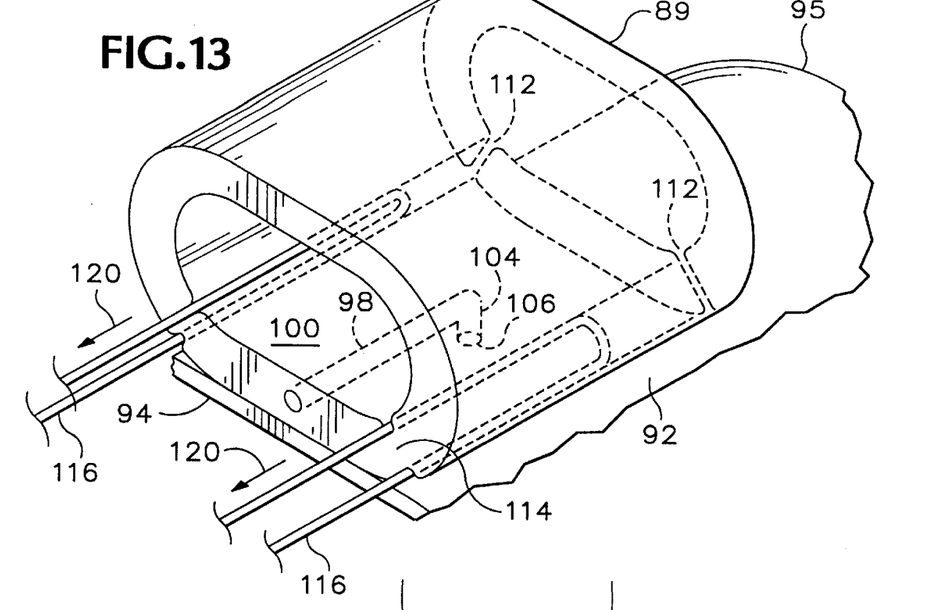
FIG. 13 is a partially cut-away view of part of the chest drain tube and probe-receiving tube shown in FIG. 8, at an enlarged scale.
Figure 14:
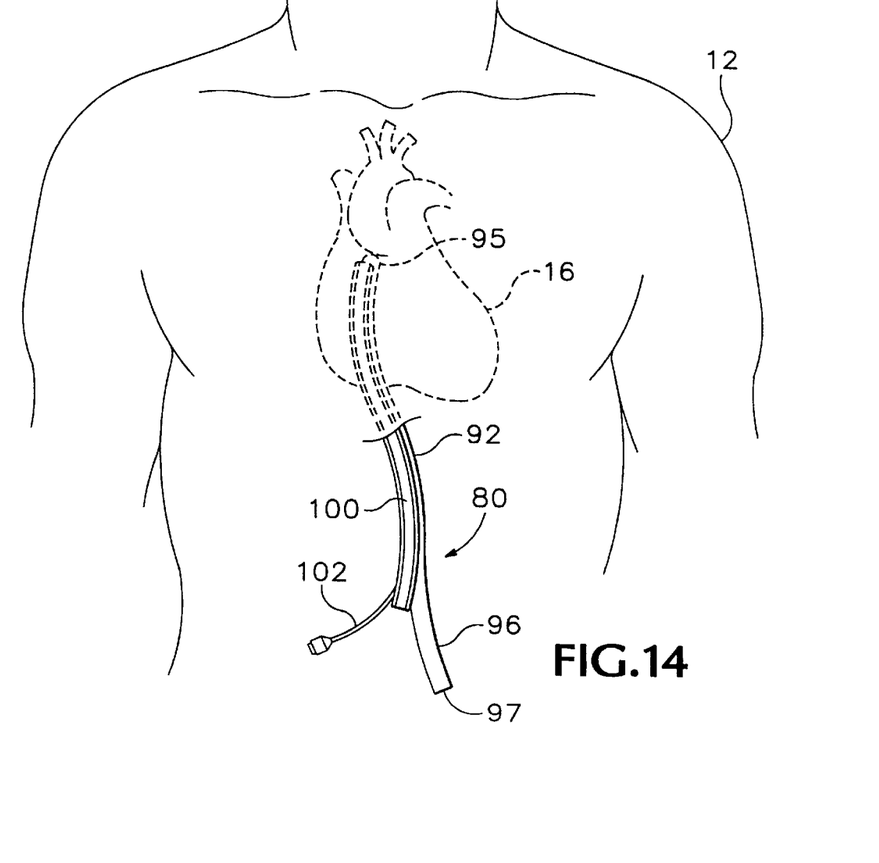
FIG. 14 is a simplified view of a patient's torso, with the device shown in FIG. 11 in place.

Preferably, however, a long U-shaped cutting element in the form of a flexible, thin, yet strong filament 116 is embedded in the wall of the drain tube 82 along each side of the base part 100 with the base of the "U" shape located in the distal end portion 88. The filament 116 may be of a synthetic fiber material of suitable tensile strength, or may be a suitably fine, flexible metal wire. At least one end of each filament 116 should be kept available near the proximal end portion 86 of the drain tube 82. The end of the filament 116 may include an attached bead-like end piece 118 to facilitate grasping at least the inner end of the filament 116 so that it can then be pulled, as indicated by the arrows 120, toward the proximal end portion 86 of the drain tube 82, causing the "U"-shaped portion to move progressively along the separation region 112 to cut free the separable part 110 of the drain tube 82, as shown in FIG. 13. The portion 122 of the proximal end portion of the drain tube 82 may easily be cut off as by scissors for convenience, to leave the base 100 as shown in FIG. 11. The base 100 thus remains as a smaller support member, more slender than the drain tube 82, and also shorter if the proximal portion 122 is removed.

In situations where it may be desired to observe the initial placement of the probe-receiving tube 92 and the attached support member radiographically, the filaments or cutting elements 116 should be of metal wire or another radiopaque material, so as to make the location of the distal end of the probe-receiving tube 92 readily apparent.

While use of a chest drain tube 82 may be necessary for a time following a surgical procedure such as a heart-valve replacement, once the drainage function is no longer required the separable portion 110 of the drain tube 82 may be removed from the base portion 100 and withdrawn from the chest cavity of the patient, leaving the base part 100 in place as a support member of reduced size attached to the probe-receiving tube 92 during a further time when it may be desired to use a sensor probe such as an ultrasound transducer. The reduced size of the support member then will promote patient comfort while preserving the possibility of quickly placing a sensor probe into the required location.

It will be understood that in other situations it may also be desirable to leave a probe-receiving tube 92 in a location where a support element of small size is sufficient once the probe-receiving tube 92 is in the required location, while a larger support member that need not be a drain tube is desired to be used during initial placement of a probe-receiving tube. A portion of such a support member may thus be removable by the use of a single cutting element 116 to leave behind a base portion 100 together with the probe-receiving tube 92 once it has been positioned appropriately.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A device for use in a medical procedure for placing a sensor probe temporarily in a desired location within a patient's body, comprising:
    (a) an elongate support member having a distal end portion and a proximal portion, said support member including a separation region defining a separable portion and a base portion; and
    (b) a thin-walled probe-receiving tube of flexible material attached to said base portion and extending closely alongside said distal end portion of said support member, said tube having a closed distal end defining an interior space within said tube.

2. The device of claim 1 including a fluid conduit extending along said base portion of said support member toward said distal end portion thereof and communicating with said interior space within said probe-receiving tube, at a location proximate said distal end.

3. The device of claim 2 wherein said elongate support member is a drain tube having a wall thicker than a wall of said distal end of said probe-receiving tube.

4. The device of claim 1 wherein said separation region has a weaker structure than adjacent portions of said support member, whereby said separable portion is easily removable from said base portion of said support member by use of force applied to said separable portion to tear apart said separation region.

5. The device of claim 1, including an elongate flexible cutting member embedded in said separation region.

6. The device of claim 5 wherein said cutting member includes a filament of a synthetic material.

7. The device of claim 5 wherein said cutting member has an end thereof that is available to be grasped at a location adjacent said proximal portion of said support member.

8. The device of claim 5 wherein said cutting member is of substantially radiopaque material.

9. The device of claim 1 wherein at least said distal portion of said probe-receiving tube is of material substantially transparent to ultrasound waves.

10. The device of claim 1 wherein said elongate support element is a drain tube for draining material from said patient's body and is of stiff, but resiliently flexible material, and wherein a distal portion of said probe-receiving tube is easily collapsible.

11. The device of claim 1 wherein said elongate support member is a chest drain tube for draining material from said patient's chest.

12. The device of claim 1 wherein said separable portion extends longitudinally of said support member from said distal portion toward said proximal portion.

13. A device for use in a medical procedure for placing a non-sterile sensor probe temporarily in a desired location within a patient's body, comprising:
   (a) an elongate support member having a sterile distal end portion and a proximal portion; and
   (b) a thin-walled probe-receiving tube having a distal portion of flexible material permanently attached to and extending closely alongside said distal end portion of said support member, said distal portion of said tube having a sterile exterior, and said tube having a closed distal end defining an interior space within said tube.

14. The device of claim 13 wherein structure attaching said probe-receiving tube to said support member is free from any structure encircling any portion of said probe-receiving tube.

15. A method for safely utilizing a non-sterile sensor probe in a desired location within a living patient, comprising:
   (a) providing a probe-receiving tube having a flexible-walled, closed distal end portion permanently attached alongside and in close proximity with a relatively stiff elongate support member having a distal portion;
   (b) thereafter inserting said distal portion of said support member together with said distal end portion of said tube into an interior cavity or a passageway into a body cavity of a living patient with said distal portion and said distal end portion in a sterile condition, leaving a proximal portion of said probe-receiving tube extending outside the patient;
   (c) temporarily inserting a sensor probe within said probe-receiving tube and into proximity with said distal end portion thereof,
   (d) placing said sensor probe in a desired location within said patient while said sensor probe is within said probe-receiving tube;
   (e) utilizing said sensor probe to make a desired observation within said patient; and
   (f) thereafter removing said sensor probe from said probe-receiving tube, while leaving said support member and said probe-receiving tube in place within said interior cavity or passageway.

16. A method for enabling a sensor probe to be placed quickly in a desired location within a living patient, comprising:
   (a) providing a probe-receiving tube having a flexible-walled, closed distal end portion permanently attached to and located alongside and in close proximity with a relatively stiff elongate support member;
   (b) thereafter inserting a distal portion of said support member together with said distal end portion of said tube into an interior cavity or a passageway communicating with a body cavity of a living patient, leaving a proximal portion of said probe-receiving tube extending outside the patient;
   (c) thereafter, temporarily inserting a sensor probe within said probe-receiving tube and into proximity with said distal end portion thereof, thereby placing said sensor probe in a desired location within said patient;
   (d) utilizing said sensor probe to make a desired observation within said patient;
   (e) thereafter removing said sensor probe from said probe-receiving tube, while leaving said support member and said probe-receiving tube in place within said interior cavity or passageway; and
   (f) removing a separable elongate part of said support member from a base part of said support member while leaving said base part and said probe-receiving tube in place within said interior cavity or passageway.

17. The method of claim 16 wherein said support member is a chest drain tube for draining material from said patient's chest cavity.

18. The method of claim 17 wherein said step of inserting includes placing said distal end portion of said probe-receiving tube in proximity with the epicardium of said patient.

19. The method of claim 16 wherein said support member is a drain tube, including the step of installing said drain tube and said probe-receiving tube during a procedure normally requiring installation of a drain tube, and including performing said step of removing a separable portion at a later time when said drain tube is no longer required, and thereafter inserting said sensor probe into proximity with an internal organ of a patient temporarily while said base portion of said drain tube remains in place.

20. The method of claim 16 wherein said sensor probe is an ultrasound transducer, including the further step of providing a quantity of an acoustic coupling fluid within said probe-receiving tube together with said ultrasound transducer.

21. The method of claim 16, including the further steps of keeping said probe-receiving tube empty and collapsed when said sensor probe is not in place within said probe-receiving tube and inserting a sensor probe into said probe-receiving tube and into proximity with said distal end portion thereof at a substantially later time.

* * * * *